US010292990B2

(12) United States Patent
Nemeth et al.

(10) Patent No.: US 10,292,990 B2
(45) Date of Patent: May 21, 2019

(54) ABIRATERONE STEROID FORMULATION

(71) Applicant: SUN PHARMA GLOBAL FZE, Sharjah (AE)

(72) Inventors: Paul Nemeth, Philadelphia, PA (US); Matt Callahan, Penn Valley, PA (US); H. William Bosch, Bryn Mawr, PA (US); Marck Norret, Darlington (AU)

(73) Assignee: SUN PHARMA GLOBAL FZE, Sharjah (AE)

(*) Notice: Subject to any disclaimer, the term of this patent is extended or adjusted under 35 U.S.C. 154(b) by 0 days.

(21) Appl. No.: 15/345,410

(22) Filed: Nov. 7, 2016

(65) Prior Publication Data
US 2017/0049788 A1 Feb. 23, 2017

Related U.S. Application Data

(63) Continuation of application No. 14/616,625, filed on Feb. 6, 2015, now abandoned, which is a continuation of application No. 14/282,535, filed on May 20, 2014, now abandoned.

(60) Provisional application No. 61/883,941, filed on Sep. 27, 2013.

(51) Int. Cl.
A61K 9/14 (2006.01)
A61K 31/58 (2006.01)
A61K 31/573 (2006.01)
A61K 45/06 (2006.01)

(52) U.S. Cl.
CPC ............ A61K 31/58 (2013.01); A61K 9/14 (2013.01); A61K 31/573 (2013.01); A61K 45/06 (2013.01)

(58) Field of Classification Search
None
See application file for complete search history.

(56) References Cited

U.S. PATENT DOCUMENTS

| | | |
|---|---|---|
| 5,478,705 A | 12/1995 | Czekai et al. |
| 5,500,331 A | 3/1996 | Czekai et al. |
| 5,604,213 A | 2/1997 | Barrie et al. |
| 6,514,524 B1 | 2/2003 | Saslawski et al. |
| 8,470,330 B2 | 6/2013 | Maddon et al. |
| 8,735,450 B2 | 5/2014 | Dodd et al. |
| 8,808,751 B2 | 8/2014 | Cammarano et al. |
| 8,822,438 B2 | 9/2014 | Auerbach et al. |
| 9,095,496 B2 | 8/2015 | Dodd et al. |
| 9,889,144 B2 | 2/2018 | Murphy et al. |
| 2007/0281934 A1 | 12/2007 | Buggy et al. |
| 2008/0004257 A1* | 1/2008 | Chan ............... C07D 403/04 514/218 |
| 2008/0051380 A1* | 2/2008 | Auerbach ............ A61K 31/58 514/176 |
| 2009/0088424 A1 | 4/2009 | Zalit et al. |
| 2009/0124587 A1 | 5/2009 | Auerbach et al. |
| 2012/0160944 A1 | 6/2012 | Dodd et al. |
| 2012/0165410 A1 | 6/2012 | Dodd et al. |
| 2013/0122085 A1* | 5/2013 | Dalton ............... A61K 31/277 424/451 |
| 2013/0277468 A1 | 10/2013 | Dodd et al. |
| 2014/0199395 A1 | 7/2014 | Dodd et al. |
| 2014/0287039 A1 | 9/2014 | Bosch et al. |
| 2015/0157646 A1 | 6/2015 | Nemeth et al. |
| 2015/0246060 A1 | 9/2015 | Murphy et al. |
| 2016/0067265 A1 | 3/2016 | Bosch et al. |
| 2017/0348328 A1 | 12/2017 | Murphy et al. |
| 2017/0354665 A1 | 12/2017 | Bosch et al. |

FOREIGN PATENT DOCUMENTS

| | | |
|---|---|---|
| CN | 101568330 A | 10/2009 |
| CN | 102743393 | 10/2012 |
| CN | 102743393 A * | 10/2012 |
| WO | WO 2008/000042 | 1/2008 |
| WO | 2008/024484 A1 | 2/2008 |
| WO | 2010/121322 A1 | 10/2010 |
| WO | 2010/121328 A1 | 10/2010 |
| WO | WO2010/121323 | 10/2010 |
| WO | WO2012/140220 | 10/2012 |
| WO | WO 2013/164473 | 11/2013 |
| WO | 2014/009434 A1 | 1/2014 |
| WO | 2014/009437 A1 | 1/2014 |
| WO | WO2014/009436 | 1/2014 |
| WO | WO 2014/009437 | 1/2014 |
| WO | WO2014/083512 | 6/2014 |
| WO | WO2014/145813 | 9/2014 |

OTHER PUBLICATIONS

Zytiga® (abiraterone acetate) Tablets, Patient Information, Janssen Biotech, Inc., © 2012, revised May 2015, 9 pages.
International Search Report and Written Opinion in corresponding PCT Application No. PCT/US14/30642, dated Aug. 12, 2014, pp. 1-13.
Janssen-Cilag International N.V., "Assessment Report for Zytiga (abiraterone) Procedure No. EMEA/H/C/002321" 2011 http://www.ema.europa.eu/docs/en_GB/document_library/EPAR_-_Public_assesment_report/human/002321/WC500112860.pdf, pp. 1-13.
Clinical trials.gov. A Comparative Study of Bioavailability of 3 New Abiraterone Acetate Tablets With Current Commercial Tablet. NCT01640093. pp. 1-3 [online]. 2013 (retrieved on Nov. 3, 2015). Retrieved from the internet URL<https://clinicaltrials.gov/ct2/show/NCT01640093?term=zytiga&rank=3>; p. 1, official title; p. 2, table.
Remington Pharmaceutical Science, 17th ed., 1985, pp. 1278-1282 and 1409-1419.
International Preliminary Report on Patentability issued in PCT/US14/30642, dated Sep. 15, 2015.

(Continued)

Primary Examiner — Susan T Tran
(74) Attorney, Agent, or Firm — Medler Ferro Woodhouse & Mills PLLC

(57) ABSTRACT

A nanoparticulate composition of abiraterone acetate that allows treatment at a lower dose than convention abiraterone acetate formulations is described as in a method of treating prostate cancer by administering the composition together with a glucocorticoid.

2 Claims, 4 Drawing Sheets

(56) References Cited

OTHER PUBLICATIONS

International Search Report issued in PCT/US15/50889, dated Dec. 17, 2015.
International Preliminary Report on Patentability issued in PCT/US15/50889, dated Mar. 21, 2017.
Non-Final Office Action Issued in U.S. Appl. No. 14/216,717, dated Feb. 11, 2015.
Non-Final Office Action issued in U.S. Appl. No. 14/823,831, dated Apr. 7, 2016.
Final Office Action issued in U.S. Appl. No. 14/523,831, dated Nov. 1, 2016.
Non-Final Office Action issued in U.S. Appl. No. 15/668,387, dated Apr. 3, 2018.
Final Office Action issued in U.S. Appl. No. 15/668,387, dated Nov. 13, 2018.
Non-Final Office Action issued in U.S. Appl. No. 14/707,922, dated Sep. 10, 2015.
Final Office Action issued in U.S. Appl. No. 14/707,922, dated Feb. 22, 2016.
Non-Final Office Action issued in U.S. Appl. No. 14/707,922, dated Oct. 3, 2016.
Final Office Action issued in U.S. Appl. No. 14/707,922, dated Jun. 9, 2017.

* cited by examiner

ABIRATERONE STEROID FORMULATION

RELATED APPLICATIONS

This application is a continuation and claims priority to U.S. application Ser. No. 14/616,625, filed Feb. 6, 2015, which is a continuation and claims priority to U.S. application Ser. No. 14/282,535, filed May 20, 2014, which claims priority to U.S. Provisional Application Ser. No. 61/883,941, filed Sep. 27, 2013, the entire contents of which are hereby referenced.

FIELD OF THE DISCLOSURE

The present disclosure relates to methods for producing particles of abiraterone acetate using dry milling processes as well as compositions comprising abiraterone acetate, medicaments produced using abiraterone acetate in nanoparticulate form and to methods of treatment of prostate cancer using a therapeutically effective amount of abiraterone acetate and a glucocorticoid.

BACKGROUND

Poor oral bioavailability is a significant problem encountered in the development of therapeutic compositions, particularly those compositions containing a drug which is poorly soluble in water at physiological pH. A drug's oral bioavailability is the degree to which the drug is absorbed into the bloodstream after oral administration. Many factors affect oral bioavailability, including the form of dosage and the solubility and dissolution rate of the drug.

In therapeutic applications, poorly water-soluble drugs tend to be eliminated from the gastrointestinal tract before being completely absorbed into the circulation. They also tend to be absorbed slowly, which can result in slow onset of therapeutic effect. In addition, poorly water-soluble drugs tend to be disfavored or even unsafe for intravenous administration due to the risk of particles of drug blocking blood flow through capillaries.

It is known that increasing the rate of dissolution of poorly soluble drugs will, in many cases, increase the rate and extent of their oral absorption. It is also known that the rate of dissolution of a particulate drug will increase with increasing surface area. One way of increasing surface area is decreasing particle size. Consequently, methods of making finely divided or sized drugs have been studied with a view to increasing the surface area and dissolution rates of drug particles used in pharmaceutical compositions.

Abiraterone 17-(3-pyridyl) androsta-5,16-dien-3β-ol) is an inhibitor CYP17 and thus interferes with the synthesis of androgens in the testes, adrenal glands and prostate tumor tissue. Abiraterone acetate, a prodrug of abiraterone, is approved in the United States for treatment of castration-resistant prostate cancer. Abiraterone acetate is considered poorly water soluble. A form of abiraterone acetate (Zytiga®) is approved in the United States for use in use in combination with prednisone for the treatment of patients with metastatic castration-resistant prostate cancer who have received prior chemotherapy containing docetaxel.

SUMMARY

The present disclosure features a method of producing a composition comprising nanoparticles of abiraterone acetate, the method comprising the steps of dry milling abiraterone acetate and a grinding matrix in a mill comprising a plurality of milling bodies, for a time period sufficient to produce nanoparticles of abiraterone acetate dispersed in an at least partially milled grinding matrix. The terms "co-grinding matrix" and "matrix" are interchangeable with "grinding matrix".

In one embodiment, the particles (nanoparticles) have a median particle size, determined on a particle volume basis, equal or less than a size selected from the group 1000 nm, 900 nm, 800 nm, 700 nm, 600 nm, 500 nm, 400 nm, 300 nm, 200 nm and 100 nm. In some embodiments, the median particle size, again on a particle volume basis, is equal to or greater than 25 nm. In some embodiments, the percentage of particles, on a particle volume basis, is selected from the group consisting of: 50%, 60%, 70%, 80%, 90%, 95% and 100% less than 1000 nm (%<1000 nm). In some embodiments, the percentage of particles, on a particle volume basis, is selected from the group consisting of: 0%, 10%, 20%, 30%, 40%, 50%, 60%, 70%, 80%, 90%, 95% and 100% less than 500 nm (%<500 nm). In some embodiments, the percentage of particles, on a particle volume basis, is selected from the group consisting of: 0%, 10%, 20%, 30%, 40%, 50%, 60%, 70%, 80%, 90%, 95% and 100% less than 300 nm (%<300 nm). In some embodiments, the percentage of particles, on a particle volume basis, is selected from the group consisting of: 0%, 10%, 20%, 30%, 40%, 50%, 60%, 70%, 80%, 90%, 95% and 100% less than 200 nm (%<200 nm). In some embodiments, the Dx of the particle size distribution, as measured on a particle volume basis, is selected from the group consisting of less than or equal to 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm, and 100 nm; wherein x is equal to 90 or is greater than or equal to 90.

In another embodiment, the crystallinity profile of the abiraterone acetate in nanoparticulate form is selected from the group consisting of: at least 50% of the abiraterone acetate is crystalline, at least 60% of the abiraterone acetate is crystalline, at least 70% of the abiraterone acetate is crystalline, at least 75% of the abiraterone acetate is crystalline, at least 85% of the abiraterone acetate is crystalline, at least 90% of the abiraterone acetate is crystalline, at least 95% of the abiraterone acetate is crystalline and at least 98% of the abiraterone acetate is crystalline. In some embodiments, the crystallinity profile of the abiraterone acetate is substantially equal to the crystallinity profile of the abiraterone acetate before the material was subjected to the method as described herein.

In another embodiment, the amorphous content of the abiraterone acetate in nanoparticulate form is selected from the group consisting of: less than 50% of the abiraterone acetate is amorphous, less than 40% of the abiraterone acetate is amorphous, less than 30% of the abiraterone acetate is amorphous, less than 25% of the abiraterone acetate is amorphous, less than 15% of the abiraterone acetate is amorphous, less than 10% of the abiraterone acetate is amorphous, less than 5% of the abiraterone acetate is amorphous and less than 2% of the abiraterone acetate is amorphous. In some embodiments, the abiraterone acetate has no significant increase in amorphous content after subjecting the material to the method as described herein.

In another embodiment, the milling time period is a range selected from the group consisting of: between 10 minutes and 2 hours, between 10 minutes and 90 minutes, between 10 minutes and 1 hour, between 10 minutes and 45 minutes, between 10 minutes and 30 minutes, between 5 minutes and 30 minutes, between 5 minutes and 20 minutes, between 2 minutes and 10 minutes, between 2 minutes and 5 minutes, between 1 minutes and 20 minutes, between 1 minute and 10 minutes, and between 1 minute and 5 minutes.

In another embodiment, the milling bodies are formed of a material selected from the group consisting of: ceramics, glasses, polymers, ferromagnetics and metals. In some embodiments, the milling bodies are steel balls having a diameter selected from the group consisting of: between 1 and 20 mm, between 2 and 15 mm and between 3 and 10 mm. In another embodiment, the milling bodies are zirconium oxide balls having a diameter selected from the group consisting of: between 1 and 20 mm, between 2 and 15 mm and between 3 and 10 mm. In some embodiments, the dry milling apparatus is a mill selected from the group consisting of: attritor mills (horizontal or vertical), nutating mills, tower mills, pearl mills, planetary mills, vibratory mills, eccentric vibratory mills, gravity-dependent-type ball mills, rod mills, roller mills and crusher mills. In some embodiments, the milling bodies within the milling apparatus are mechanically agitated by 1, 2 or 3 rotating shafts. Preferably, the method is configured to produce the abiraterone acetate in a continuous fashion.

In another embodiment, the grinding matrix is a single material or is a mixture of two or more materials in any proportion. In some embodiments, the single material or a mixture of two or more materials is selected from the group consisting of: mannitol, sorbitol, Isomalt, xylitol, maltitol, lactitol, erythritol, arabitol, ribitol, glucose, fructose, mannose, galactose, anhydrous lactose, lactose monohydrate, sucrose, maltose, trehalose, and maltodextrins. In some embodiments the single material or mixture of two or more materials is selected from the group consisting of: dextrin, Inulin, dextrates, polydextrose, starch, wheat flour, corn flour, rice flour, rice starch, tapioca flour, tapioca starch, potato flour, potato starch, other flours and starches, milk powder, skim milk powders, other milk solids and dreviatives, soy flour, soy meal or other soy products, cellulose, microcrystalline cellulose, microcrystalline cellulose based co-blended materials, pregelatinized (or partially) starch, HPMC, CMC, HPC, citric acid, tartaric acid, malic acid, maleic acid fumaric acid, ascorbic acid, succinic acid, sodium citrate, sodium tartrate, sodium malate, sodium ascorbate, potassium citrate, potassium tartrate, potassium malate, sodium acetate, potassium ascorbate, sodium carbonate, potassium carbonate, magnesium carbonate, sodium bicarbonate, potassium bicarbonate, calcium carbonate, dibasic calcium phosphate, tribasic calcium phosphate, sodium sulfate, sodium chloride, sodium metabisulphite, sodium thiosulfate, ammonium chloride, glauber's salt, ammonium carbonate, sodium bisulfate, magnesium sulfate, potash alum, potassium chloride, sodium hydrogen sulfate, sodium hydroxide, crystalline hydroxides, hydrogen carbonates, ammonium chloride, methylamine hydrochloride, ammonium bromide, silica, thermal silica, alumina, titanium dioxide, talc, chalk, mica, kaolin, bentonite, hectorite, magnesium trisilicate, clay based materials or aluminium silicates, sodium lauryl sulfate, sodium stearyl sulfate, sodium cetyl sulfate, sodium cetostearyl sulfate, sodium docusate, sodium deoxycholate, N-lauroylsarcosine sodium salt, glyceryl monostearate, glycerol distearate glyceryl palmitostearate, glyceryl behenate, glyceryl caprylate, glyceryl oleate, benzalkonium chloride, CTAB, CTAC, Cetrimide, cetylpyridinium chloride, cetylpyridinium bromide, benzethonium chloride, PEG 40 stearate, PEG 100 stearate, poloxamer 188, poloxamer 338, poloxamer 407 polyoxyl 2 stearyl ether, polyoxyl 100 stearyl ether, polyoxyl 20 stearyl ether, polyoxyl 10 stearyl ether, polyoxyl 20 cetyl ether, polysorbate 20, polysorbate 40, polysorbate 60, polysorbate 61, polysorbate 65, polysorbate 80, polyoxyl 35 castor oil, polyoxyl 40 castor oil, polyoxyl 60 castor oil, polyoxyl 100 castor oil, polyoxyl 200 castor oil, polyoxyl 40 hydrogenated castor oil, polyoxyl 60 hydrogenated castor oil, polyoxyl 100 hydrogenated castor oil, polyoxyl 200 hydrogenated castor oil, cetostearyl alcohol, macrogel 15 hydroxystearate, sorbitan monopalmitate, sorbitan monostearate, sorbitan trioleate, sucrose palmitate, sucrose stearate, sucrose distearate, sucrose laurate, glycocholic acid, sodium glycholate, cholic acid, soidum cholate, sodium deoxycholate, deoxycholic acid, sodium taurocholate, taurocholic acid, sodium taurodeoxycholate, taurodeoxycholic acid, soy lecithin, phosphatidylcholine, phosphatidylethanolamine, phosphatidylserine, phosphatidylinositol, PEG4000, PEG6000, PEG8000, PEG10000, PEG20000, alkyl naphthalene sulfonate condensate/Lignosulfonate blend, calcium dodecylbenzene sulfonate, sodium dodecylbenzene sulfonate, diisopropyl naphthaenesulphonate, erythritol distearate, naphthalene sulfonate formaldehyde condensate, nonylphenol ethoxylate (poe-30), tristyrylphenol ethoxylate, polyoxyethylene (15) tallowalkylamines, sodium alkyl naphthalene sulfonate, sodium alkyl naphthalene sulfonate condensate, sodium alkylbenzene sulfonate, sodium isopropyl naphthalene sulfonate, sodium methyl naphthalene formaldehyde sulfonate, sodium n-butyl naphthalene sulfonate, tridecyl alcohol ethoxylate (poe-18), triethanolamine isodecanol phosphate ester, triethanolamine tristyrylphosphate ester, tristyrylphenol ethoxylate sulfate, bis(2-hydroxyethyptallowalkylamines.

In some embodiments, the concentration of the single (or first) grinding matrix is selected from the group consisting of: 5-99% w/w, 10-95% w/w, 15-85% w/w, of 20-80% w/w, 25-75% w/w, 30-60% w/w, 40-50% w/w. In some embodiments, the concentration of the second or subsequent grinding matrix is selected from the group consisting of: 5-50% w/w, 5-40% w/w, 5-30% w/w, of 5-20% w/w, 10-40% w/w, 10-30% w/w, 10-20% w/w, 20-40% w/w, or 20-30% w/w or if the second or subsequent material is a surfactant or water soluble polymer the concentration is selected from 0.1-10% w/w, 0.1-5% w/w, 0.1-2.5% w/w, of 0.1-2% w/w, 0.1-1%, 0.5-5% w/w, 0.5-3% w/w, 0.5-2% w/w, 0.5-1.5%, 0.5-1% w/w, of 0.75-1.25% w/w, 0.75-1% and 1% w/w.

In some embodiments, the grinding matrix is selected from the group consisting of:
(a) lactose monohydrate or lactose monohydrate combined with at least one material selected from the group consisting of: xylitol; lactose anhydrous; microcrystalline cellulose; sucrose; glucose; sodium chloride; talc; kaolin; calcium carbonate; malic acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(b) lactose anhydrous or lactose anhydrous combined with at least one material selected from the group consisting of: lactose monohydrate; xylitol; microcrystalline cellulose; sucrose; glucose; sodium chloride; talc; kaolin; calcium carbonate; malic acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(c) mannitol or mannitol combined with at least one material selected from the group consisting of: lactose monohydrate; xylitol; lactose anhydrous; microcrystalline cellulose; sucrose; glucose; sodium chloride; talc; kaolin; calcium carbonate; malic acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(d) Sucrose or sucrose combined with at least one material selected from the group consisting of: lactose monohydrate; lactose anhydrous; mannitol; microcrystalline cellulose; glucose; sodium chloride; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyphtallowalkylamines.

(e) Glucose or glucose combined with at least one material selected from the group consisting of: lactose monohydrate; lactose anhydrous; mannitol; microcrystalline cellulose; sucrose; sodium chloride; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(f) Sodium chloride or sodium chloride combined with at least one material selected from the group consisting of: lactose monohydrate; lactose anhydrous; mannitol; microcrystalline cellulose; sucrose; glucose; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(g) xylitol or xylitol combined with at least one material selected from the group consisting of: lactose monohydrate; lactose anhydrous; mannitol; microcrystalline cellulose; sucrose; glucose; sodium chloride; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(h) Tartaric acid or tartaric acid combined with at least one material selected from the group consisting of: lactose monohydrate; lactose anhydrous; mannitol; microcrystalline cellulose; sucrose; glucose; sodium chloride; talc; kaolin; calcium carbonate; malic acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(i) microcrystalline cellulose or microcrystalline cellulose combined with at least one material selected from the group consisting of: lactose monohydrate; xylitol; lactose anhydrous; mannitol; sucrose; glucose; sodium chloride; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

(j) Kaolin combined with at least one material selected from the group consisting of: lactose monohydrate; xylitol; lactose anhydrous; mannitol; microcrystalline cellulose; sucrose; glucose; sodium chloride; talc; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyptallowalkylamines.

(k) Talc combined with at least one material selected from the group consisting of: lactose monohydrate; xylitol; lactose anhydrous; mannitol; microcrystalline cellulose; sucrose; glucose; sodium chloride; kaolin; calcium carbonate; malic acid; tartaric acid; trisodium citrate dihydrate; D,L-Malic acid; sodium pentane sulfate; sodium octadecyl sulfate; Brij700; Brij76; sodium n-lauroyl sacrosine; lecithin; docusate sodium; polyoxyl-40-stearate; Aerosil R972 fumed silica; sodium lauryl sulfate or other alkyl sulfate surfactants with a chain length between C5 to C18; polyvinyl pyrrolidone; sodium lauryl sulfate and polyethylene glycol 40 stearate, sodium lauryl sulfate and polyethylene glycol 100 stearate, sodium lauryl sulfate and PEG 3000, sodium lauryl sulphate and PEG 6000, sodium lauryl sulphate and PEG 8000, sodium lauryl sulphate and PEG 10000, sodium lauryl sulfate and Brij700, sodium lauryl sulfate and Poloxamer 407, sodium lauryl sulfate and Poloxamer 338, sodium lauryl sulfate and Poloxamer 188; Poloxamer 407, Poloxamer 338, Poloxamer 188, alkyl naphthalene sulfonate condensate/Lignosulfonate blend; Calcium Dodecylbenzene Sulfonate (Branched); Diisopropyl naphthalenesulphonate; erythritol distearate; linear and branched dodecylbenzene sulfonic acids; Naphthalene Sulfonate Formaldehyde Condensate; nonylphenol ethoxylate, POE-30; Phosphate Esters, Tristyrylphenol Ethoxylate, Free Acid; Polyoxyethylene (15) tallowalkylamines; sodium alkyl naphthalene sulfonate; sodium alkyl naphthalene sulfonate condensate; sodium alkylbenzene sulfonate; sodium isopropyl naphthalene sulfonate; Sodium Methyl Naphthalene; Formaldehyde Sulfonate; sodium salt of n-butyl naphthalene sulfonate; tridecyl alcohol ethoxylate, POE-18; Triethanolamine isodecanol phosphate ester; Triethanolamine tristyrylphosphate ester; Tristyrylphenol Ethoxylate Sulfate; Bis(2-hydroxyethyl)tallowalkylamines.

In some embodiments, the grinding matrix is selected from the group consisting of: a material considered 'Generally Regarded as Safe' (GRAS) for pharmaceutical products; a material considered acceptable for use in an agricultural formulation; and a material considered acceptable for use in a veterinary formulation.

In another embodiment, a facilitating agent or combination of facilitating agents is used. In some embodiments, the milling aid is selected from the group consisting of: colloidal silica, a surfactant, a polymer, a stearic acid and derivatives thereof. In some embodiments, the surfactant is selected from the group consisting of: polyoxyethylene alkyl ethers, polyoxyethylene stearates, polyethylene glycols (PEG), poloxamers, poloxamines, sarcosine based surfactants, polysorbates, aliphatic alcohols, alkyl and aryl sulfates, alkyl and aryl polyether sulfonates and other sulfate surfactants, trimethyl ammonium based surfactants, lecithin and other phospholipids, bile salts, polyoxyethylene castor oil derivatives, polyoxyethylene sorbitan fatty acid esters, Sorbitan fatty acid esters, Sucrose fatty acid esters, alkyl glucopyranosides, alkyl maltopyranosides, glycerol fatty acid esters, Alkyl Benzene Sulphonic Acids, Alkyl Ether Carboxylic Acids, Alkyl and aryl Phosphate esters, Alkyl and aryl Sulphate esters, Alkyl and aryl Sulphonic acids, Alkyl Phenol Phosphates esters, Alkyl Phenol Sulphates esters, Alkyl and Aryl Phosphates, Alkyl Polysaccharides, Alkylamine Ethoxylates, Alkyl-Naphthalene Sulphonates formaldehyde condensates, Sulfosuccinates, lignosulfonates, Ceto-Oleyl Alcohol Ethoxylates, Condensed Naphthalene Sulphonates, Dialkyl and Alkyl Naphthalene Sulphonates, Di-alkyl Sulphosuccinates, Ethoxylated nonylphenols, Ethylene Glycol Esters, Fatty Alcohol Alkoxylates, Hydrogenated tallowalkylamines, Mono-alkyl Sulphosuccinamates, Nonyl Phenol Ethoxylates, Sodium Oleyl N-methyl Taurate, Tallowalkylamines, linear and branched dodecylbenzene sulfonic acids.

In some embodiments, the surfactant is selected from the group consisting of: sodium lauryl sulfate, sodium stearyl sulfate, sodium cetyl sulfate, sodium cetostearyl sulfate, sodium docusate, sodium deoxycholate, N-lauroylsarcosine sodium salt, glyceryl monostearate, glycerol distearate glyceryl palmitostearate, glyceryl behenate, glyceryl caprylate, glyceryl oleate, benzalkonium chloride, CTAB, CTAC, Cetrimide, cetylpyridinium chloride, cetylpyridinium bromide, benzethonium chloride, PEG 40 stearate, PEG 100 stearate, poloxamer 188, poloxamer 338, poloxamer 407 polyoxyl 2 stearyl ether, polyoxyl 100 stearyl ether, polyoxyl 20 stearyl ether, polyoxyl 10 stearyl ether, polyoxyl 20 cetyl ether, polysorbate 20, polysorbate 40, polysorbate 60, polysorbate 61, polysorbate 65, polysorbate 80, polyoxyl 35 castor oil, polyoxyl 40 castor oil, polyoxyl 60 castor oil, polyoxyl 100 castor oil, polyoxyl 200 castor oil, polyoxyl 40 hydrogenated castor oil, polyoxyl 60 hydrogenated castor oil, polyoxyl 100 hydrogenated castor oil, polyoxyl 200 hydrogenated castor oil, cetostearyl alcohol, macrogel 15 hydroxystearate, sorbitan monopalmitate, sorbitan monostearate, sorbitan trioleate, Sucrose Palmitate, Sucrose Stearate, Sucrose Distearate, Sucrose laurate, Glycocholic acid, sodium Glycholate, Cholic Acid, Soidum Cholate, Sodium Deoxycholate, Deoxycholic acid, Sodium taurocholate, taurocholic acid, Sodium taurodeoxycholate, taurodeoxycholic acid, soy lecithin, phosphatidylcholine, phosphatidylethanolamine, phosphatidylserine, phosphatidylinositol, PEG4000, PEG6000, PEG8000, PEG10000, PEG20000, alkyl naphthalene sulfonate condensate/Lignosulfonate blend, Calcium Dodecylbenzene Sulfonate, Sodium Dodecylbenzene Sulfonate, Diisopropyl naphthaenesulphonate, erythritol distearate, Naphthalene Sulfonate Formaldehyde Condensate, nonylphenol ethoxylate (poe-30), Tristyrylphenol Ethoxylate, Polyoxyethylene (15) tallowalkylamines, sodium alkyl naphthalene sulfonate, sodium alkyl naphthalene sulfonate condensate, sodium alkylbenzene sulfonate, sodium isopropyl naphthalene sulfonate, Sodium Methyl Naphthalene Formaldehyde Sulfonate, sodium n-butyl naphthalene sulfonate, tridecyl alcohol ethoxylate (poe-18), Triethanolamine isodecanol phosphate ester, Triethanolamine tristyrylphosphate ester, Tristyrylphenol Ethoxylate Sulfate, Bis(2-hydroxyethyl)tallowalkylamines.

In some embodiments the facilitating agent is selected from the list of: polyvinylpyrrolidones (PVP), polyvinylalcohol, acrylic acid based polymers and copolymers of acrylic acid.

In some embodiments, the milling aid has a concentration selected from the group consisting of: 0.1-10% w/w, 0.1-5% w/w, 0.1-2.5% w/w, of 0.1-2% w/w, 0.1-1%, 0.5-5% w/w, 0.5-3% w/w, 0.5-2% w/w, 0.5-1.5%, 0.5-1% w/w, of 0.75-1.25% w/w, 0.75-1% and 1% w/w. In another embodiment of the disclosure, a facilitating agent is used or combination of facilitating agents is used. In some embodiments, the facilitating agent is added during dry milling. In some embodiments, the facilitating agent is added to the dry milling at a time selected from the group consisting of: with 1-5% of the total milling time remaining, with 1-10% of the total milling time remaining, with 1-20% of the total milling time remaining, with 1-30% of the total milling time remaining, with 2-5% of the total milling time remaining, with 2-10% of the total milling time remaining, with 5-20% of the total milling time remaining and with 5-20% of the total milling time remaining. In some embodiments, the disintegrant is selected from the group consisting of: crosslinked PVP, cross linked carmellose and sodium starch glycolate. In some embodiments, the facilitating agent is added to the milled abiraterone acetate and grinding matrix and further processed in a mechanofusion process. Mechanofusion milling causes mechanical energy to be applied to powders or mixtures of particles in the micrometer and nanometer range.

The reasons for including facilitating agents include, but are not limited to providing better dispersibility, control of agglomeration, the release or retention of the active particles from the delivery matrix. Examples of facilitating agents include, but are not limited to crosslinked PVP (crospovidone), cross linked sodium carboxymethylcellulose (croscarmellose sodium), sodium starch glycolate, povidone (PVP), Povidone K12, Povidone K17, Povidone K25, Povidone K29/32 and Povidone K30, stearic acid, magnesium stearate, calcium stearate, sodium stearyl fumarate, sodium stearyl lactylate, zinc stearate, sodium stearate or lithium stearate, other solid state fatty acids such as oleic acid, lauric acid, palmitic acid, erucic acid, behenic acid, or derivatives (such as esters and salts), Amino acids such as leucine, isoleucine, lysine, valine, methionine, phenylalanine, aspartame or acesulfame K.

In some embodiments, abiraterone acetate is milled with one or more grinding matrixes selected from the group consisting of; lactose (e.g., lactose monohyrdrate), mannitol and sodium chloride and one or more facilitating agents selected from povidone and sodium lauryl sulphate. In some cases, abiraterone acetate is milled with lactose (e.g., lactose monohyrdrate), sodium lauryl sulphate and povidone. In some cases during dry milling the abiraterone acetate can be present at 20-30% (w/w) the lactose at up to 77% (w/w) the mannitol at up to 77% (w/w), the sodium chloride at p to 15% (w/w) and the povidone and sodium lauryl sulfact each (or both) at 1-3% (w/w).

In one embodiment, the disclosure comprises compositions comprising abiraterone acetate together with a grinding matrix, a mixture of grinding matrix materials, milling aids, mixtures of milling aids, facilitating agents and/or mixtures of facilitating agents as described herein, in concentrations and ratios as described herein under the methods of the disclosure.

In some embodiments, the disclosure comprises pharmaceutical compositions comprising abiraterone acetate prepared using the dry milling methods described herein together with a grinding matrix, a mixture of grinding matrix materials, milling aids, mixtures of milling aids, facilitating agents and/or mixtures of facilitating agents as described herein, in concentrations and ratios as described herein under the methods of the disclosure In some embodiments, the particles have a median particle size, determined on a particle volume basis, equal or less than a size selected from the group 1000 nm, 900 nm, 800 nm, 700 nm, 600 nm, 500 nm, 400 nm, 300 nm, 200 nm and 100 nm. In some embodiments, the median particle size is equal to or greater than 25 nm. In some embodiments, the percentage of particles, on a particle volume basis, is selected from the group consisting of: less than 1000 nm (%<1000 nm) is selected from the group consisting of: 50%, 60%, 70%, 80%, 90%, 95% and 100%; less than 500 nm (%<500 nm) is selected from the group 0%, 10%, 20%, 30%, 40%, 50%, 60%, 70%, 80%, 90%, 95% and 100%; less than 300 nm (%<300 nm) is selected from the group 0%, 10%, 20%, 30%, 40%, 50%, 60%, 70%, 80%, 90%, 95% and 100%; and less than 200 nm (%<200 nm) is selected from the group 0%, 10%, 20%, 30%, 40%, 50%, 60%, 70%, 80%, 90%, 95% and 100%.

In some embodiments, an abiraterone acetate composition of the present disclosure has a $T_{max}$ less than that of a conventional composition (Zytiga®) when both compositions are administered at the same dosage. In some embodiments, an abiraterone acetate of the present disclosure has a $C_{max}$ greater than that of a conventional composition when both compositions are administered at the same dosage, wherein the composition comprises abiraterone acetate. In some embodiments, an abiraterone acetate of the present disclosure has an AUC greater than that of a conventional composition when both compositions are administered at the same dosage, wherein the composition comprises abiraterone acetate. In some embodiments, an abiraterone acetate of the present disclosure has a $T_{max}$ less than that of a conventional composition when the composition of the present disclosure is administered at a lower dosage, wherein the composition comprises abiraterone acetate. In some embodiments, an abiraterone acetate of the present invention has a $C_{max}$ greater than or equal to that of a conventional composition when the abiraterone acetate of the present disclosure is administered at a lower dosage. In some embodiments, a composition of the present disclosure has an AUC greater than or equal to that of a conventional composition when the composition of the present disclosure is administered at a lower dosage, wherein the composition comprises abiraterone acetate.

Importantly, the abiraterone acetate composition of the present disclosure has reduced food effect compared to Zytiga®.

In another aspect the disclosure comprises a method of treating a human in need of such treatment comprising the step of administering to the human an effective amount of a pharmaceutical composition as described herein for treatment of castration resistant prostate cancer and administering to a patient that is also being treated with a glucocorticoid (e.g., prednisone, prednisolone, methylprednisolone or dexamethasone. It is also possible to use In another aspect, the disclosure comprises the use of a pharmaceutical composition as described herein in the manufacture of a medicament for the treatment of a human in need of such treatment.

In another aspect the disclosure comprises a method for manufacturing a pharmaceutical composition as described herein comprising the step of combining a therapeutically effective amount of a abiraterone acetate prepared by a method described herein or a composition as described herein, together with a pharmaceutically acceptable carrier to produce a pharmaceutically acceptable dosage form.

Other aspects and advantages of the disclosure will become apparent to those skilled in the art from a review of the ensuing description.

DETAILED DESCRIPTION OF THE DISCLOSURE

General

Those skilled in the art will appreciate that the disclosure described herein is susceptible to variations and modifications other than those specifically described. It is to be understood that the disclosure includes all such variations and modifications. The disclosure also includes all of the steps, features, compositions and materials referred to or indicated in the specification, individually or collectively and any and all combinations or any two or more of the steps or features.

The present disclosure is not to be limited in scope by the specific embodiments described herein, which are intended for the purpose of exemplification only. Functionally equivalent products, compositions and methods are clearly within the scope of the disclosure as described herein.

The disclosure described herein may include one or more ranges of values (e.g. size, concentration etc). A range of values will be understood to include all values within the range, including the values defining the range, and values adjacent to the range that lead to the same or substantially the same outcome as the values immediately adjacent to that value which defines the boundary to the range.

The entire disclosures of all publications (including patents, patent applications, journal articles, laboratory manuals, books, or other documents) cited herein are hereby incorporated by reference. Inclusion does not constitute an admission is made that any of the references constitute prior art or are part of the common general knowledge of those working in the field to which this disclosure relates.

Throughout this specification, unless the context requires otherwise, the word "comprise" or variations, such as "comprises" or "comprising" will be understood to imply the inclusion of a stated integer, or group of integers, but not the exclusion of any other integers or group of integers. It is also noted that in this disclosure, and particularly in the claims and/or paragraphs, terms such as "comprises", "comprised", "comprising" and the like can have the meaning attributed to it in US Patent law; e.g., they can mean "includes", "included", "including", and the like.

"Therapeutically effective amount" as used herein with respect to methods of treatment and in particular drug dosage, shall mean that dosage that provides the specific pharmacological response for which the drug is administered in a significant number of subjects in need of such treatment. It is emphasized that "therapeutically effective amount," administered to a particular subject in a particular instance will not always be effective in treating the diseases described herein, even though such dosage is deemed a "therapeutically effective amount" by those skilled in the art. It is to be further understood that drug dosages are, in particular instances, measured as oral dosages, or with reference to drug levels as measured in blood.

The term "inhibit" is defined to include its generally accepted meaning which includes prohibiting, preventing, restraining, and lowering, stopping, or reversing progression or severity, and such action on a resultant symptom. As such the present disclosure includes both medical therapeutic and prophylactic administration, as appropriate.

The term "grinding matrix" is defined as any inert substance that a biologically active material can be or is combined with and milled. The terms "co-grinding matrix" and "matrix" are interchangeable with "grinding matrix".

Particle Size

There are a wide range of techniques that can be utilized to characterize the particle size of a material. Those skilled in the art also understand that almost all these techniques do not physically measure the actually particle size, as one might measure something with a ruler, but measure a physical phenomena which is interpreted to indicate a particle size. As part of the interpretation process some assumptions need to be made to enable mathematical calculations to be made. These assumptions deliver results such as an equivalent spherical particle size, or a hydrodynamic radius.

Amongst these various methods, two types of measurements are most commonly used. Photon correlation spectroscopy (PCS), also known as 'dynamic light scattering' (DLS) is commonly used to measure particles with a size less than 10 micron. Typically this measurement yields an equivalent hydrodynamic radius often expressed as the average size of a number distribution. The other common particle size measurement is laser diffraction which is commonly used to measure particle size from 100 nm to 2000 micron. This technique calculates a volume distribution of equivalent spherical particles that can be expressed using descriptors such as the median particle size or the % of particles under a given size.

Those skilled in the art recognize that different characterization techniques such as photon correlation spectroscopy and laser diffraction measure different properties of a particle ensemble. As a result multiple techniques will give multiple answers to the question, "what is the particle size." In theory one could convert and compare the various parameters each technique measures, however, for real world particle systems this is not practical. As a result the particle size used to describe this disclosure will be given as two different sets of values that each relate to these two common measurement techniques, such that measurements could be made with either technique and then evaluated against the description of this disclosure.

For measurements made using a photo correlation spectroscopy instrument, or an equivalent method known in the art, the term "number average particle size" is defined as the average particle diameter as determined on a number basis.

For measurements made using a laser diffraction instrument, or an equivalent method known in the art, the term "median particle size" is defined as the median particle diameter as determined on an equivalent spherical particle volume basis. Where the term median is used, it is understood to describe the particle size that divides the population in half such that 50% of the population is greater than or less than this size. The median particle size is often written as D50, D(0.50) or D[0.5] or similar. As used herein D50, D(0.50) or D[0.5] or similar shall be taken to mean 'median particle size'.

The term "Dx of the particle size distribution" refers to the xth percentile of the distribution; thus, D90 refers to the $90^{th}$ percentile, D95 refers to the $95^{th}$ percentile, and so forth. Taking D90 as an example this can often be written as, D(0.90) or D[0.9] or similar. With respect to the median particle size and Dx an upper case D or lowercase d are interchangeable and have the same meaning. Another commonly used way of describing a particle size distribution measured by laser diffraction, or an equivalent method known in the art, is to describe what % of a distribution is under or over a nominated size. The term "percentage less than" also written as "%<" is defined as the percentage, by volume, of a particle size distribution under a nominated size—for example the %<1000 nm. The term "percentage greater than" also written as "%>" is defined as the percentage, by volume, of a particle size distribution over a nominated size—for example the %>1000 nm.

The particle size used to describe this disclosure should be taken to mean the particle size as measured at or shortly before the time of use. For example, the particle size is measured 2 months after the material is subject to the milling method of this disclosure. In a form, the particle size is measured at a time selected from the group consisting of: 1 day after milling, 2 days after milling, 5 days after milling, 1 month after milling, 2 months after milling, 3 months after milling, 4 months after milling, 5 months after milling, 6 months after milling, 1 year after milling, 2 years after milling, 5 years after milling.

For many of the materials subject to the methods of this disclosure the particle size can be easily measured. Where the active material has poor water solubility and the matrix it is milled in has good water solubility the powder can simply be dispersed in an aqueous solvent. In this scenario the matrix dissolves leaving the active material dispersed in the solvent. This suspension can then be measured by techniques such as PCS or laser diffraction.

Suitable methods to measure an accurate particle size where the active material has substantive aqueous solubility or the matrix has low solubility in a water based dispersant are outlined below.

1. In the circumstance where insoluble matrix such as microcrystalline cellulose prevents the measurement of the active material separation techniques such as filtration or centrifugation could be used to separate the insoluble matrix from the active material particles. Other ancillary techniques would also be required to determine if any active material was removed by the separation technique so that this could be taken into account.
2. In the case where the active material is too soluble in water other solvents could be evaluated for the measurement of particle size. Where a solvent could be found that active material is poorly soluble in but is a good solvent for the matrix a measurement would be relatively straight forward. If such a solvent is difficult to find another approach would be to measure the ensemble of matrix and active material in a solvent (such as iso-octane) which both are insoluble in. Then the powder would be measured in another solvent where the active material is soluble but the matrix is not. Thus with a measurement of the matrix particle size and a measurement of the size of the matrix and active material together an understanding of the active material particle size can be obtained.
3. In some circumstances image analysis could be used to obtain information about the particle size distribution of the active material. Suitable image measurement techniques might include transmission electron microscopy (TEM), scanning electron microscopy (SEM), optical microscopy and confocal microscopy. In addition to these standard techniques some additional technique would be required to be used in parallel to differentiate the active material and matrix particles. Depending on the chemical makeup of the materials involved possible techniques could be elemental analysis, raman spectroscopy, FTIR spectroscopy or fluorescence spectroscopy.

Other Definitions

Throughout this specification, unless the context requires otherwise, the phrase "dry mill" or variations, such as "dry milling", should be understood to refer to milling in at least the substantial absence of liquids. If liquids are present, they are present in such amounts that the contents of the mill retain the characteristics of a dry powder.

"Flowable" means a powder having physical characteristics rendering it suitable for further processing using typical equipment used for the manufacture of pharmaceutical compositions and formulations.

Other definitions for selected terms used herein may be found within the detailed description of the disclosure and apply throughout. Unless otherwise defined, all other scientific and technical terms used herein have the same meaning as commonly understood to one of ordinary skill in the art to which the disclosure belongs.

The term "millable" means that the grinding matrix is capable of being reduced in size under the dry milling conditions of the method of the disclosure. In one embodiment of the disclosure, the milled grinding matrix is of a comparable particle size to the abiraterone acetate. In another embodiment of the disclosure the particle size of the matrix is substantially reduced but not as small as the abiraterone acetate Other definitions for selected terms used herein may be found within the detailed description of the disclosure and apply throughout. Unless otherwise defined, all other scientific and technical terms used herein have the same meaning as commonly understood to one of ordinary skill in the art to which the disclosure belongs.

DRAWINGS

Specific

Figure 1:
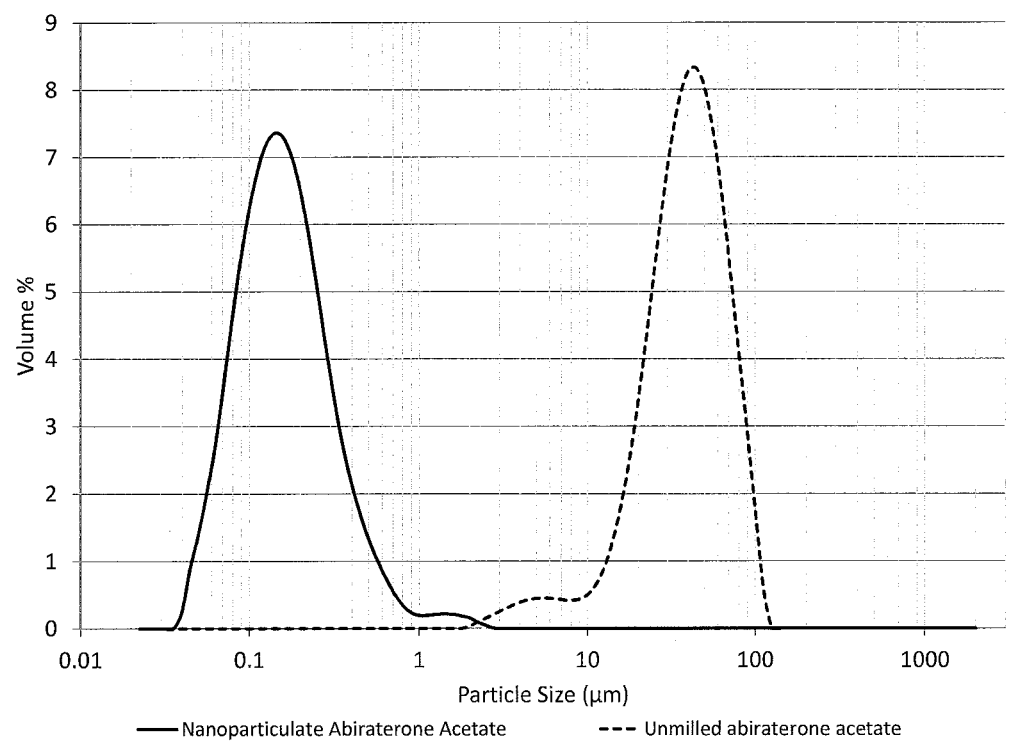
FIG. 1 is a graph depicting the size distribution of abiraterone acetate in a milled arbiraterone acetate composition from Example 1 and unmilled abiraterone acetate.

In one embodiment, the present disclosure is directed to a method for producing a composition, comprising the steps of: dry milling abiraterone acetate and a millable grinding matrix in a mill comprising a plurality of milling bodies, for a time period sufficient to produce particles of the abiraterone acetate dispersed in an at least partially milled grinding material.

The mixture of active material and matrix may then be separated from the milling bodies and removed from the mill.

In one aspect the mixture of active material and matrix is then further processed. In another aspect, the grinding matrix is separated from the particles of abiraterone acetate.

In a further aspect, at least a portion of the milled grinding matrix is separated from the particulate abiraterone acetate.

The milling bodies are essentially resistant to fracture and erosion in the dry milling process. The quantity of the grinding matrix relative to the quantity of abiraterone acetate in particulate form, and the extent of milling of the grinding matrix, is sufficient to inhibit re-agglomeration of the particles of the active material.

Improving the Dissolution Profile

The process results in the abiraterone acetate having an improved dissolution profile. An improved dissolution profile has significant advantages including the improvement of bioavailability of the abiraterone acetate in vivo. In some embodiments, the improved dissolution profile is observed in vitro. Alternatively, the improved dissolution profile is observed in vivo by the observation of an improved bioavailability profile. Standard methods for determining the dissolution profile of a material in vitro are available in the art. A suitable method to determine an improved dissolution profile in vitro may include determining the concentration of the sample material in a solution over a period of time and comparing the results from the sample material to a control sample. An observation that peak solution concentration for the sample material was achieved in less time than the control sample would indicate (assuming it is statistically significant), that the sample material has an improved dissolution profile. The measurement sample is herein defined as the mixture of abiraterone acetate with grinding matrix and/or other additives that has been subject to the processes of the disclosure described here. Herein a control sample is defined as a physical mixture (not subject to the processes described in this disclosure) of the components in the measurement sample with the same relative proportions of active, matrix and/or additive as the measurement sample. For the purposes of the dissolution testing a prototype formulation of the measurement sample could also be used. In this case the control sample would be formulated in the same way. Standard methods for determining the improved dissolution profile of a material in vivo are available in the art. A suitable method to determine an improved dissolution profile in a human may be after delivering the dose to measure the rate of active material absorption by measuring the plasma concentration of the sample compound over a period of time and comparing the results from the sample compound to a control. An observation that peak plasma concentration for the sample compound was achieved in less time than the control would indicate (assuming it is statistically significant) that the sample compound has improved bioavailability and an improved dissolution profile. In some embodiments, the improved dissolution profile is observed at a relevant gastrointestinal pH, when it is observed in vitro. In some embodiments, the improved dissolution profile is observed at a pH which is favourable at indicating improvements in dissolution when comparing the measurement sample to the control compound. Suitable methods for quantifying the concentration of a compound in an in vitro sample or an in vivo sample are widely available in the art. Suitable methods could include the use of spectroscopy or radioisotope labeling. In one embodiment the method of quantification of dissolution is determined in a solution with a pH selected from the group consisting of: pH 1, pH 2, pH 3, pH 4, pH 5, pH 6, pH 7, pH 7.3, pH 7.4, pH 8, pH 9, pH 10, pH 11, pH 12, pH 13, pH 14 or a pH with 0.5 of a pH unit of any of this group.

Crystallization Profile

Methods for determining the crystallinity profile of the abiraterone acetate are widely available in the art. Suitable methods may include X-ray diffraction, differential scanning calorimetry, Raman or IR spectrocopy.

Amorphicity Profile

Methods for determining the amorphous content of the abiraterone acetate are widely available in the art. Suitable methods may include X-ray diffraction, differential scanning calorimetry, Raman or IR spectroscopy.

Grinding Matrix

As will be described subsequently, selection of an appropriate grinding matrix affords particular advantageous applications of the method of the present disclosure.

Again, as will be described subsequently, a highly advantageous aspect of the present disclosure is that certain grinding matrixes appropriate for use in the method of the disclosure are also appropriate for use in a medicament. The present disclosure encompasses methods for the production of a medicament incorporating both the abiraterone acetate and the grinding matrix or in some cases the abiraterone acetate and a portion of the grinding matrix, medicaments so produced, and methods of treatment of an animal, including man, using a therapeutically effective amount of said abiraterone acetates by way of said medicaments.

The medicament may include only the abiraterone acetate together with the milled grinding matrix or, more preferably, the abiraterone acetate and milled grinding matrix may be combined with one or more pharmaceutically acceptable carriers, as well as any desired excipients or other like agents commonly used in the preparation of medicaments.

In one particular form of the disclosure, the grinding matrix is both appropriate for use in a medicament and readily separable from the abiraterone acetate by methods not dependent on particle size. Such grinding matrixes are described in the following detailed description of the disclosure. Such grinding matrixes are highly advantageous in that they afford significant flexibility in the extent to which the grinding matrix may be incorporated with the abiraterone acetate into a medicament.

In some cases the grinding matrix is harder than the abiraterone acetate, and is thus capable of reducing the particle size of the abiraterone acetate under the dry milling conditions of the disclosure. Again without wishing to be bound by theory, under these circumstances it is believed that the millable grinding matrix affords the advantage of the present disclosure through a second route, with the smaller particles of grinding matrix produced under the dry milling conditions enabling greater interaction with the abiraterone acetate.

The quantity of the grinding matrix relative to the quantity of abiraterone acetate, and the extent of physical degradation of the grinding matrix, is sufficient to inhibit re-agglomeration of the particles of the active material In some embodiments, the quantity of the grinding matrix relative to the quantity of abiraterone acetate, and the extent of physical degradation of the grinding matrix, is sufficient to inhibit re-agglomeration of the particles of the active material in nanoparticulate form. The grinding matrix is not generally selected to be chemically reactive with the abiraterone acetate under the milling conditions of the disclosure, excepting for example, where the matrix is deliberately chosen to undergo a mechanico-chemical reaction. Such a reaction might be the conversion of a free base or acid to a salt or vice versa.

As stated above, the method of the present disclosure requires the grinding matrix to be milled with the abiraterone acetate; that is, the grinding matrix will physically degrade under the dry milling conditions of the disclosure to facilitate the formation and retention of particulates of the abiraterone acetate with reduced particle size. The precise extent of degradation required will depend on certain properties of the grinding matrix and the abiraterone acetate, the ratio of abiraterone acetate to grinding matrix, and the particle size distribution of the particles comprising the abiraterone acetate.

In some embodiments, the grinding matrix has a low tendency to agglomerate during dry milling. While it is difficult to objectively quantify the tendency to agglomerate during milling, it is possible to obtain a subjective measure by observing the level of "caking" of the grinding matrix on the milling bodies and the milling chamber of the media mill as dry milling progresses.

The grinding matrix may be an inorganic or organic substance.

Milling Bodies

In the method of the present disclosure, the milling bodies are preferably chemically inert and rigid. The term "chemically-inert", as used herein, means that the milling bodies do not react chemically with the abiraterone acetate or the grinding matrix.

As described above, the milling bodies are essentially resistant to fracture and erosion in the milling process.

The milling bodies are desirably provided in the form of bodies which may have any of a variety of smooth, regular shapes, flat or curved surfaces, and lacking sharp or raised edges. For example, suitable milling bodies can be in the form of bodies having ellipsoidal, ovoid, spherical or right cylindrical shapes. In some embodiments, the milling bodies are provided in the form of one or more of beads, balls, spheres, rods, right cylinders, drums or radius-end right cylinders (i.e., right cylinders having hemispherical bases with the same radius as the cylinder).

Depending on the nature of the abiraterone acetate and the grinding matrix, the milling bodies desirably have an effective mean particle diameter (i.e. "particle size") between about 0.1 and 30 mm, more preferably between about 1 and about 15 mm, still more preferably between about 3 and 10 mm.

The milling bodies may comprise various substances such as ceramic, glass, metal or polymeric compositions, in a particulate form. Suitable metal milling bodies are typically spherical and generally have good hardness (i.e. RHC 60-70), roundness, high wear resistance, and narrow size distribution and can include, for example, balls fabricated from type 52100 chrome steel, type 316 or 440C stainless steel or type 1065 high carbon steel.

Ceramics, for example, can be selected from a wide array of ceramics desirably having sufficient hardness and resistance to fracture to enable them to avoid being chipped or crushed during milling and also having sufficiently high density. Suitable densities for milling bodies can range from about 1 to 15 g/cm$^3$, preferably from about 1 to 8 g/cm$^3$. Ceramics can be selected from steatite, aluminum oxide, zirconium oxide, zirconia-silica, yttria-stabilized zirconium oxide, magnesia-stabilized zirconium oxide, silicon nitride, silicon carbide, cobalt-stabilized tungsten carbide, and the like, as well as mixtures thereof.

Glass milling bodies are spherical (e.g. beads), have a narrow size distribution, are durable, and include, for example, lead-free soda lime glass and borosilicate glass. Polymeric milling bodies are preferably substantially spherical and can be selected from a wide array of polymeric resins having sufficient hardness and friability to enable them to avoid being chipped or crushed during milling, abrasion-resistance to minimize attrition resulting in contamination of the product, and freedom from impurities such as metals, solvents, and residual monomers.

Milling bodies can be formed from polymeric resins. Polymeric resins, for example, can be selected from cross-linked polystyrenes, such as polystyrene crosslinked with divinylbenzene, styrene copolymers, polyacrylates such as polymethylmethacrylate, polycarbonates, polyacetals, vinyl chloride polymers and copolymers, polyurethanes, polyamides, high density polyethylenes, polypropylenes, and the like. The use of polymeric milling bodies to grind materials down to a very small particle size (as opposed to mechano-chemical synthesis) is disclosed, for example, in U.S. Pat. Nos. 5,478,705 and 5,500,331. Polymeric resins typically can have densities ranging from about 0.8 to 3.0 g/cm$^3$. Higher density polymeric resins are. Alternatively, the milling bodies can be composite bodies comprising dense core bodies having a polymeric resin adhered thereon. Core particles can be selected from substances known to be useful as milling bodies, for example, glass, alumina, zirconia silica, zirconium oxide, stainless steel, and the like. Core substances have densities greater than about 2.5 g/cm$^3$.

In one embodiment of the disclosure, the milling bodies are formed from a ferromagnetic substance, thereby facilitating removal of contaminants arising from wear of the milling bodies by the use of magnetic separation techniques.

Each type of milling body has its own advantages. For example, metals have the highest specific gravities, which increase grinding efficiency due to increased impact energy. Metal costs range from low to high, but metal contamination of final product can be an issue. Glasses are advantageous from the standpoint of low cost and the availability of small bead sizes as low as 0.004 mm. However, the specific gravity of glasses is lower than other bodies and significantly more milling time is required. Finally, ceramics are advantageous from the standpoint of low wear and contamination, ease of cleaning, and high hardness.

Dry Milling

In the dry milling process of the present disclosure, the abiraterone acetate and grinding matrix, in the form of crystals, powders, or the like, are combined in suitable proportions with the plurality of milling bodies in a milling chamber that is mechanically agitated (i.e. with or without stirring) for a predetermined period of time at a predetermined intensity of agitation. Typically, a milling apparatus is used to impart motion to the milling bodies by the external application of agitation, whereby various translational, rotational or inversion motions or combinations thereof are applied to the milling chamber and its contents, or by the internal application of agitation through a rotating shaft terminating in a blade, propeller, impeller or paddle or by a combination of both actions.

During milling, motion imparted to the milling bodies can result in application of shearing forces as well as multiple impacts or collisions having significant intensity between milling bodies and particles of the abiraterone acetate and grinding matrix. The nature and intensity of the forces applied by the milling bodies to the abiraterone acetate and the grinding matrix is influenced by a wide variety of processing parameters including: the type of milling apparatus; the intensity of the forces generated, the kinematic aspects of the process; the size, density, shape, and composition of the milling bodies; the weight ratio of the abiraterone acetate and grinding matrix mixture to the milling bodies; the duration of milling; the physical properties of both the abiraterone acetate and the grinding matrix; the atmosphere present during activation; and others.

Advantageously, the media mill is capable of repeatedly or continuously applying mechanical compressive forces and shear stress to the abiraterone acetate and the grinding matrix. Suitable media mills include but are not limited to the following: high-energy ball, sand, bead or pearl mills, basket mill, planetary mill, vibratory action ball mill, multi-axial shaker/mixer, stirred ball mill, horizontal small media mill, multi-ring pulverizing mill, and the like, including small milling media. The milling apparatus also can contain one or more rotating shafts.

In a form of the disclosure, the dry milling is performed in a ball mill. Throughout the remainder of the specification reference will be made to dry milling being carried out by way of a ball mill. Examples of this type of mill are attritor mills, nutating mills, tower mills, planetary mills, vibratory mills and gravity-dependent-type ball mills. It will be appreciated that dry milling in accordance with the method of the disclosure may also be achieved by any suitable means other than ball milling. For example, dry milling may also be achieved using jet mills, rod mills, roller mills or crusher mills.

In some cases, the particle size of the abiraterone acetate prior to dry milling according to the methods described herein in less than about 1000 μm, as determined by sieve analysis. If the particle size of the abiraterone acetate is greater than about 1000 μm, then it is preferred that the particles of the abiraterone acetate substrate be reduced in size to less than 1000 μm using another standard milling method prior to dry milling according to the methods described herein.

Processed Abiraterone Acetate

In some embodiments, the abiraterone acetate, which has been subject to the methods of the disclosure, comprises particles of abiraterone acetate of a median particle size, determined on a particle volume basis, equal or less than a size selected from the 1000 nm, 900 nm, 800 nm, 700 nm, 600 nm, 500 nm, 400 nm, 300 nm, 200 nm and 100 nm.

In some embodiments, the abiraterone acetate, which has been subject to the methods of the disclosure, comprises particles of abiraterone acetate and wherein the Dx of the particle size distribution, as measured on a particle volume basis, is selected from the group consisting of less than or equal to 2000 nm, 1900 nm, 1800 nm, 1700 nm, 1600 nm, 1500 nm, 1400 nm, 1300 nm, 1200 nm, 1100 nm, 1000 nm, 900 nm, 800 nm, 700 nm, 600 nm, 500 nm, 400 nm, 300 nm, 200 nm, and 100 nm; wherein x is equal to 90 or is greater than or equal to 90.

Agglomerates of Abiraterone Acetate after Processing

Agglomerates comprising particles of abiraterone acetate, said particles having a particle size within the ranges specified above, should be understood to fall within the scope of the present disclosure, regardless of whether the agglomerates exceed the ranges specified above. Agglomerates comprising particles of abiraterone acetate, said agglomerates having a total agglomerate size within the ranges specified above, should be understood to fall within the scope of the present disclosure.

Agglomerates comprising particles of abiraterone acetate should be understood to fall within the scope of the present disclosure if at the time of use, or further processing, the particle size of the agglomerate is within the ranges specified above.

Agglomerates comprising particles of abiraterone acetate, said particles having a particle size within the ranges specified above, at the time of use, or further processing, should be understood to fall within the scope of the present disclosure, regardless of whether the agglomerates exceed the ranges specified above.

Processing Time

In some embodiments, the abiraterone acetate and the grinding matrix are dry milled for the shortest time necessary to minimise any possible contamination from the media mill and/or the plurality of milling bodies. This time varies greatly, depending on the abiraterone acetate and the grinding matrix, and may range from as short as 1 minute to several hours. Dry milling times in excess of 2 hours may lead to degradation of the abiraterone acetate and an increased level of undesirable contaminants.

Suitable rates of agitation and total milling times are adjusted for the type and size of milling apparatus as well as the milling media, the weight ratio of the abiraterone acetate and grinding matrix mixture to the plurality of milling bodies, the chemical and physical properties of the abiraterone acetate and grinding matrix, and other parameters that may be optimized empirically.

Inclusion of the Grinding Matrix with the Abiraterone Acetate and Separation of the Grinding Matrix from the Abiraterone Acetate In some embodiments, the grinding matrix is not separated from the abiraterone acetate but is maintained with the abiraterone acetate in the final product. In some embodiments the grinding matrix is considered to be Generally Regarded as Safe (GRAS) for pharmaceutical products. In an alternative aspect, the grinding matrix is separated from the abiraterone acetate. In one aspect, where the grinding matrix is not fully milled, the unmilled grinding matrix is separated from the abiraterone acetate. In a further aspect, at least a portion of the milled grinding matrix is separated from the abiraterone acetate.

Any portion of the grinding matrix may be removed, including but not limited to 10%, 25%, 50%, 75%, or substantially all of the grinding matrix.

In some embodiments of the disclosure, a significant portion of the milled grinding matrix may comprise particles of a size similar to and/or smaller than the particles comprising the abiraterone acetate. Where the portion of the milled grinding matrix to be separated from the particles comprising the abiraterone acetate comprises particles of a size similar to and/or smaller than the particles comprising the abiraterone acetate, separation techniques based on size distribution are inapplicable. In these circumstances, the method of the present disclosure may involve separation of at least a portion of the milled grinding matrix from the abiraterone acetate by techniques including but not limited to electrostatic separation, magnetic separation, centrifugation (density separation), hydrodynamic separation, froth flotation. Advantageously, the step of removing at least a portion of the milled grinding matrix from the abiraterone acetate may be performed through means such as selective dissolution, washing, or sublimation.

An advantageous aspect of the disclosure would be the use of grinding matrix that has two or more components where at least one component is water soluble and at least one component has low solubility in water. In this case washing can be used to remove the matrix component soluble in water leaving the abiraterone acetate dispersed in the remaining matrix components. In a highly advantageous aspect of the disclosure the matrix with low solubility is a functional excipient.

A highly advantageous aspect of the present disclosure is that certain grinding matrixes appropriate for use in the method of the disclosure (in that they physically degrade to the desired extent under dry milling conditions) are also pharmaceutically acceptable and thus appropriate for use in a medicament. Where the method of the present disclosure does not involve complete separation of the grinding matrix from the abiraterone acetate, the present disclosure encompasses methods for the production of a medicament incorporating both the abiraterone acetate and at least a portion of the milled grinding matrix, medicaments so produced and methods of treatment of an animal, including man, using a therapeutically effective amount of said abiraterone acetate by way of said medicaments.

The medicament may include only the abiraterone acetate and the grinding matrix or, more preferably, the abiraterone acetate and grinding matrix may be combined with one or more pharmaceutically acceptable carriers, as well as any desired excipients or other like agents commonly used in the preparation of medicaments.

In one particular form of the disclosure, the grinding matrix is both appropriate for use in a medicament and readily separable from the abiraterone acetate by methods not dependent on particle size. Such grinding matrixes are described in the following detailed description of the disclosure. Such grinding matrixes are highly advantageous in that they afford significant flexibility in the extent to which the grinding matrix may be incorporated with the abiraterone acetate into a medicament.

The mixture of abiraterone acetate and grinding matrix may then be separated from the milling bodies and removed from the mill.

In one embodiment, the grinding matrix is separated from the mixture of abiraterone acetate and grinding matrix. Where the grinding matrix is not fully milled, the unmilled grinding matrix is separated from the abiraterone acetate. In a further aspect, at least a portion of the milled grinding matrix is separated from the abiraterone acetate.

The milling bodies are essentially resistant to fracture and erosion in the dry milling process.

The quantity of the grinding matrix relative to the quantity of abiraterone acetate, and the extent of milling of the grinding matrix, is sufficient to provide reduced particle size of the abiraterone acetate.

The grinding matrix is neither chemically nor mechanically reactive with the pharmaceutical material under the dry milling conditions of the method of the disclosure In some embodiments, the medicament is a solid dosage form, however, other dosage forms may be prepared by those of ordinary skill in the art.

In one form, after the step of separating said mixture of abiraterone acetate and grinding matrix from the plurality of milling bodies, and before the step of using said mixture of abiraterone acetate and grinding matrix in the manufacture of a medicament, the method may comprise the step of: removing a portion of the grinding matrix from said mixture of abiraterone acetate and grinding matrix to provide a mixture enriched in the abiraterone acetate; and the step of using said mixture of abiraterone acetate and grinding matrix in the manufacture of a medicament, more particularly comprises the step of using the mixture of abiraterone acetate and grinding matrix enriched in the abiraterone acetate form in the manufacture of a medicament.

The present disclosure includes medicaments manufactured by said methods, and methods for the treatment of an animal, including man, by the administration of a therapeutically effective amount of abiraterone acetate by way of said medicaments.

Abiraterone Acetate and Compositions

The present disclosure encompasses pharmaceutically acceptable materials produced according to the methods of the present disclosure, compositions including such materials, including compositions comprising such materials together with the grinding matrix with or without milling aids, facilitating agents, with at least a portion of the grinding matrix or separated from the grinding matrix.

The pharmaceutically acceptable materials within the compositions of the disclosure are present at a concentration of between about 0.1% and about 99.0% by weight. In some embodiments, the concentration of pharmaceutically acceptable materials within the compositions will be about 5% to about 80% by weight, while concentrations of 10% to about 50% by weight are highly. Desirably, the concentration will be in the range of about 10 to 15% by weight, 15 to 20% by weight, 20 to 25% by weight, 25 to 30% by weight, 30 to 35% by weight, 35 to 40% by weight, 40 to 45% by weight, 45 to 50% by weight, 50 to 55% by weight, 55 to 60% by weight, 60 to 65% by weight, 65 to 70% by weight, 70 to 75% by weight or 75 to 80% by weight for the composition prior to any later removal (if desired) of any portion of the grinding matrix. Where part or all of the grinding matrix has been removed, the relative concentration of pharmaceutically acceptable materials in the composition may be considerably higher depending on the amount of the grinding matrix that is removed. For example, if all of the grinding matrix is removed the concentration of particles in the preparation may approach 100% by weight (subject to the presence of facilitating agents).

Compositions produced according to the present disclosure are not limited to the inclusion of a single species of pharmaceutically acceptable materials. More than one species of pharmaceutically acceptable materials may therefore be present in the composition. Where more than one species of pharmaceutically acceptable materials is present, the composition so formed may either be prepared in a dry milling step, or the pharmaceutically acceptable materials may be prepared separately and then combined to form a single composition.

Medicaments

The medicaments of the present disclosure may include the pharmaceutically acceptable material, optionally together with the grinding matrix or at least a portion of the grinding matrix, with or without milling aids, facilitating agents, combined with one or more pharmaceutically acceptable carriers, as well as other agents commonly used in the preparation of pharmaceutically acceptable compositions.

As used herein "pharmaceutically acceptable carrier" includes any and all solvents, dispersion media, coatings, antibacterial and antifungal agents, isotonic and absorption delaying agents, and the like that are physiologically compatible. In some embodiments, the carrier is suitable for parenteral administration, intravenous, intraperitoneal, intramuscular, sublingual, pulmonary, transdermal or oral administration. Pharmaceutically acceptable carriers include sterile aqueous solutions or dispersions and sterile powders for the extemporaneous preparation of sterile injectable solutions or dispersion. The use of such media and agents for the manufacture of medicaments is well known in the art. Except insofar as any conventional media or agent is incompatible with the pharmaceutically acceptable material, use thereof in the manufacture of a pharmaceutical composition according to the disclosure is contemplated.

Pharmaceutical acceptable carriers according to the disclosure may include one or more of the following examples:

(1) surfactants and polymers including, but not limited to polyethylene glycol (PEG), polyvinylpyrrolidone (PVP), polyvinylalcohol, crospovidone, polyvinylpyrrolidone-polyvinylacrylate copolymer, cellulose derivatives, hydroxypropylmethyl cellulose, hydroxypropyl cellulose, carboxymethylethyl cellulose, hydroxypropyllmethyl cellulose phthalate, polyacrylates and polymethacrylates, urea, sugars, polyols, and their polymers, emulsifiers, sugar gum, starch, organic acids and their salts, vinyl pyrrolidone and vinyl acetate (2) binding agents such as various celluloses and cross-linked polyvinylpyrrolidone, microcrystalline cellulose; and or (3) filling agents such as lactose monohydrate, lactose anhydrous, microcrystalline cellulose and various starches; and or (4) lubricating agents such as agents that act on the flowability of the powder to be compressed, including colloidal silicon dioxide, talc, stearic acid, magnesium stearate, calcium stearate, silica gel; and or (5) sweeteners such as any natural or artificial sweetener including sucrose, xylitol, sodium saccharin, cyclamate, aspartame, and accsulfame K; and or (6) flavouring agents; and or (7) preservatives such as potassium sorbate, methylparaben, propylparaben, benzoic acid and its salts, other esters of parahydroxybenzoic acid such as butylparaben, alcohols such as ethyl or benzyl alcohol, phenolic chemicals such as phenol, or quarternary compounds such as benzalkonium chloride; and or (8) buffers; and or (9) Diluents such as pharmaceutically acceptable inert fillers, such as microcrystalline cellulose, lactose, dibasic calcium phosphate, saccharides, and/or mixtures of any of the foregoing; and or

(10) wetting agents such as corn starch, potato starch, maize starch, and modified starches, and mixtures thereof; and or

(11) disintegrants; such as croscarmellose sodium, crospovidone, sodium starch glycolate, and or

(12) effervescent agents such as effervescent couples such as an organic acid (e.g., citric, tartaric, malic, fumaric, adipic, succinic, and alginic acids and anhydrides and acid salts), or a carbonate (e.g. sodium carbonate, potassium carbonate, magnesium carbonate, sodium glycine carbonate, L-lysine carbonate, and arginine carbonate) or bicarbonate (e.g. sodium bicarbonate or potassium bicarbonate); and or

(13) other pharmaceutically acceptable excipients.

Actual dosage levels of abiraterone acetate disclosure may be varied in accordance with the nature of the abiraterone acetate, as well as the potential increased efficacy due to the advantages of providing and administering the abiraterone acetate (e.g., increased solubility, more rapid dissolution, increased surface area of the abiraterone acetate, etc.). Thus as used herein "therapeutically effective amount" will refer to an amount of abiraterone acetate required to effect a therapeutic response in an animal. Amounts effective for such a use will depend on: the desired therapeutic effect; the route of administration; the potency of the abiraterone acetate; the desired duration of treatment; the stage and severity of the disease being treated; the weight and general state of health of the patient; and the judgment of the prescribing physician.

Pharmacokinetic Properties of Abiraterone acetate Compositions

Fast Onset of Activity

The abiraterone acetate compositions of the disclosure are more rapidly absorbed. In one example, following administration the abiraterone acetate compositions of the disclosure comprising abiraterone acetate have a $T_{max}$ of less than about 5 hours, less than about 4.5 hours, less than about 4 hours, less than about 3.5 hours, less than about 3 hours, less than about 2.75 hours, less than about 2.5 hours, less than about 2.25 hours, less than about 2 hours, less than about 1.75 hours, less than about 1.5 hours, less than about 1.25 hours, less than about 1.0 hours, less than about 50 minutes, less than about 40 minutes, less than about 30 minutes, less than about 25 minutes, less than about 20 minutes, less than about 15 minutes, less than about 10 minutes, less than about 5 minutes, or less than about 1 minute.

Increased Bioavailability

The abiraterone acetate compositions of the disclosure preferably exhibit increased bioavailability (AUC) and require smaller doses as compared to prior conventional compositions administered at the same dose. Any drug composition can have adverse side effects. Thus, lower doses of drugs which can achieve the same or better therapeutic effects as those observed with larger doses of conventional compositions are desired. Such lower doses can be realized with the compositions of the disclosure because the greater bioavailability observed with the compositions as compared to conventional drug formulations means that smaller doses of drug are required to obtain the desired therapeutic effect.

The Pharmacokinetic Profiles of the Compositions of the Disclosure are not Substantially Affected by the Fed or Fasted State of the Subject Ingesting the Compositions The disclosure encompasses abiraterone acetate compositions wherein the pharmacokinetic profile of the composition is not substantially affected by the fed or fasted state of a subject ingesting the composition. This means that there is no substantial difference in the quantity of composition or the rate of composition absorption when the compositions are administered in the fed versus the fasted state. Thus, the compositions of the disclosure substantially eliminate the effect of food on the pharmacokinetics of the composition.

The difference in absorption of the abiraterone acetate composition of the disclosure, when administered in the fed versus the fasted state, is less than about 100%, less than about 50%, less than about 35%, less than about 30%, less than about 25%, less than about 20%, less than about 15%, less than about 10%, less than about 5%, or less than about 3%. This is an especially important feature in treating patients with difficulty in maintaining a fed state. In comparative pharmacokinetic testing with a standard conventional drug active composition, an abiraterone acetate composition of the disclosure exhibits less variability than the standard composition. Variability may be quantified by mathematical terms such as standard deviation, coefficient of variation, or other suitable measure. A composition of the disclosure is expected to show less variability in Tmax, Cmax, AUC(0-t), AUC(0-∞) relative to a standard composition. A composition of the disclosure is also expected to show less variability in the average plasma concentration at any given time point after administration relative to a standard composition.

An abiraterone acetate composition of the disclosure causes relevant biomarkers such as androgen levels, prostate-specific antigen (PSA) levels, and circulating tumor cell (CTC) concentrations to decrease more rapidly after administration relative to a standard composition.

In addition, preferably the difference in the rate of absorption (i.e., $T_{max}$) of the abiraterone acetate compositions of the disclosure, when administered in the fed versus the fasted state, is less than about 100%, less than about 90%, less than about 80%, less than about 70%, less than about 60%, less than about 50%, less than about 40%, less than about 30%, less than about 20%, less than about 15%, less than about 10%, less than about 5%, less than about 3%, or essentially no difference. Benefits of a dosage form which substantially eliminates the effect of food include an increase in subject convenience, thereby increasing subject compliance, as the subject does not need to ensure that they are taking a dose either with or without food.

In some embodiments, the $T_{max}$ of an administered dose of an abiraterone acetate composition of the disclosure is less than that of a conventional drug active composition, administered at the same dosage.

An abiraterone acetate composition of the disclosure exhibits in comparative pharmacokinetic testing with a standard conventional drug active composition, in oral suspension, capsule or tablet form, a $T_{max}$ which is less than about 100%, less than about 90%, less than about 80%, less than about 70%, less than about 60%, less than about 50%, less than about 40%, less than about 30%, less than about 25%, less than about 20%, less than about 15%, or less than about 10% of the $T_{max}$ exhibited by the standard conventional drug active composition.

In addition, preferably the $C_{max}$ of a abiraterone acetate composition of the disclosure is greater than the $C_{max}$ of a conventional drug active composition (e.g., Zytiga), administered at the same dosage. An abiraterone acetate composition of the disclosure exhibits in comparative pharmacokinetic testing with a standard conventional drug active composition (e.g., Zytiga), in oral suspension, capsule or tablet form, a Cmax which is greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, or greater than about 150% than the $C_{max}$ exhibited by the standard conventional drug active composition when administered at equivalent doses. In some cases the abiraterone acetate composition has a Cmax greater than or equal to that of a conventional composition when administered at a dose less than or equal to 90% of the conventional dose of the conventional composition (e.g., Zytiga), at a dose less than or equal to 80% of the conventional dose of the conventional composition), or at dose less than or equal to 70% of the conventional dose of the conventional composition when administered at equivalent doses.

In addition, preferably the abiraterone acetate composition has an AUC greater than that of the equivalent conventional composition administered at the same dosage. An abiraterone acetate composition of the disclosure exhibits in comparative pharmacokinetic testing with a standard conventional drug active composition, in oral suspension, capsule or tablet form, a AUC which is greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, or greater than about 150% than the AUC exhibited by the standard conventional drug active composition.

Any standard pharmacokinetic protocol can be used to determine blood plasma concentration profile in humans following administration of a composition, and thereby establish whether that composition meets the pharmacokinetic criteria set out herein. For example, a randomized single-dose crossover study can be performed using a group of healthy adult human subjects. The number of subjects should be sufficient to provide adequate control of variation in a statistical analysis, and is typically about 10 or greater, although for certain purposes a smaller group can suffice. Each subject receives by oral administration at time zero a single dose (e.g., 300 mg) of a test formulation of composition, normally at around 8 am following an overnight fast. The subjects continue to fast and remain in an upright position for about 4 hours after administration of the composition. Blood samples are collected from each subject prior to administration (e.g., 15 minutes) and at several intervals after administration. For the present purpose it is to take several samples within the first hour, and to sample less frequently thereafter. Illustratively, blood samples could be collected at 15, 30, 45, 60, and 90 minutes after administration, then every hour from 2 to 10 hours after administration. Additional blood samples may also be taken later, for example at 12 and 24 hours after administration. If the same subjects are to be used for study of a second test formulation, a period of at least 7 days should elapse before administration of the second formulation. Plasma is separated from the blood samples by centrifugation and the separated plasma is analyzed for composition by a validated high performance liquid chromatography (HPLC) or liquid chromatography mass spectrometry (LCMS) procedure. Plasma concentrations of composition referenced herein are intended to mean total concentrations including both free and bound composition.

Any formulation giving the desired pharmacokinetic profile is suitable for administration according to the present methods. Exemplary types of formulations giving such profiles are liquid dispersions and solid dose forms of composition. If the liquid dispersion medium is one in which the composition has very low solubility, the particles are present as suspended particles.

Thus, a abiraterone acetate composition of the disclosure, upon administration to a subject, provides improved pharmacokinetic and/or pharmacodynamic properties compared with a standard reference abiraterone acetate composition as measured by at least one of speed of absorption, dosage potency, efficacy, and safety.

Modes of Administration of Medicaments Comprising Abiraterone Acetates

Medicaments of the disclosure can be administered to animals, including man, in any pharmaceutically acceptable manner, such as orally, rectally, pulmonary, intravaginally, locally (powders, ointments or drops), transdermal, parenteral administration, intravenous, intraperitoneal, intramuscular, sublingual or as a buccal or nasal spray.

Solid dosage forms for oral administration include capsules, tablets, pills, powders, pellets, and granules. Further, incorporating any of the normally employed excipients, such as those previously listed, and generally 5-95% of the biologically active agent, and more preferably at a concentration of 10%-75% will form a pharmaceutically acceptable non-toxic oral composition.

As described above, the abiraterone acetate can be formulated into a solid dosage form (e.g., for oral or suppository administration), together with the grinding matrix or at least a portion of it. In this case there may be little or no need to add stabilizing agents since the grinding matrix may effectively act as a solid-state stabilizer.

However, if the abiraterone acetate is to be utilized in a liquid suspension, the particles comprising the abiraterone acetate may require further stabilization once the solid carrier has been substantially removed to ensure the elimination, or at least minimisation of particle agglomeration.

EXAMPLE 1. PREPARATION OF NANOPARTICULATE ABIRATERONE ACETATE

Abiraterone acetate drug substance was obtained from Hangzhao Dayangchem Co., Ltd.; Hangzhao City, P.R. China. A mixture (3.0 g) of abiraterone acetate (10% w/w), lactose monohydrate (89%; DMV Fonterra), and sodium lauryl sulfate (1%; Sigma-Aldrich) was milled in a Spex vibratory mill for 10 minutes to yield 2.7 g of nanoparticulate abiraterone acetate. The particle size distributions of unmilled abiraterone acetate and nanoparticulate abiraterone acetate were determined by light scattering techniques (Malvern Mastersizer 2000); the average particle size of the unmilled material was approximately 40 μm (volume statistics; $D_{10}$=16 μm, $D_{50}$=37 μm; $D_{90}$=70 μm) whereas the average size of the nanoparticulate abiraterone acetate drug particles was approximately 1000 nm ($D_{10}$=75 nm; $D_{50}$=177 nm; $D_{90}$=2.5 μm). The results are depicted graphically in FIG. 1 (below).

EXAMPLE 2. COMPARATIVE DISSOLUTION STUDIES

Approximately 250 mg of the nanoparticulate abiraterone acetate formulation prepared in Example 1 (corresponding to 25 mg of active ingredient) was hand-filled into size 1 hard gelatin capsules. Also, 250 mg of unmilled abiraterone acetate was hand filled into similar capsules. Dissolution profiles were measured in triplicate using a Varian VK7025 dissolution apparatus fitted with (6) 1000 mL vessels, with detection performed in a Varian UV-Vis Spectrophotometer at 270 nm. Each vessel contained 900 mL dissolution media consisting of 10 mmol phosphate buffer at pH 6 with 0.1% SDS added. Experiments were conducted at 37° C. The hard gelatin capsules were fitted inside spiral sinkers before commencing the dissolution experiments.

Figure 2:
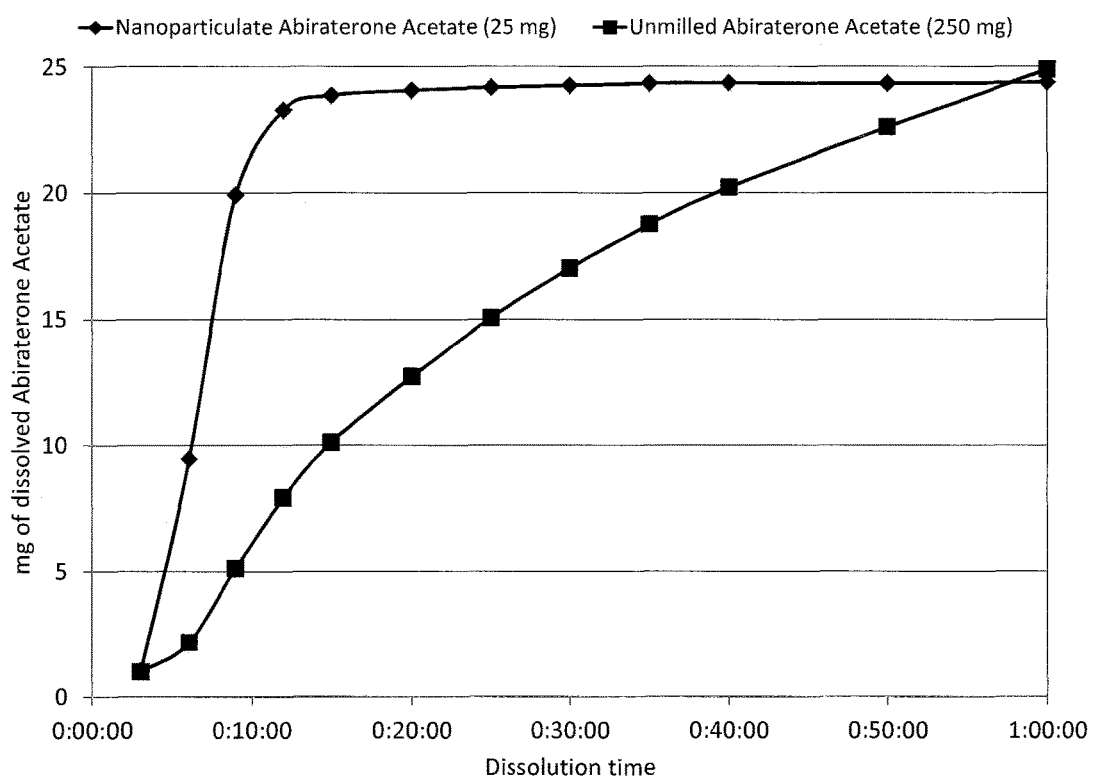
FIG. 2 is a graph depicting the dissolution of abiraterone acetate in a milled arbiraterone acetate composition from Example 1 and unmilled abiraterone acetate.

The results indicate that under the conditions studied, only approximately 10% of the unmilled abiraterone acetate (25 mg) is dissolved after one hour, while 100% of the nanoparticulate abiraterone acetate the dissolution (25 mg) is dissolved within approximately 10 minutes (FIG. 2).

EXAMPLE 3. PREPARATION OF NANOPARTICULATE ABIRATERONE ACETATE

Abiraterone acetate was obtained from Chongquing Pharmaceutical Research Institute (China). Lactose Monohydrate NF was obtained from Meggle Pharma (CapsuLac® 60). Sodium lauryl sulfate NF was obtained from Cognis (Texapon® K12 P PH). A SPEX Sample Prep 5100 Mixer Mill (Metuchen, N.J.) with a 2.5 ml stainless steel grinding vial and two ¼" stainless steel grinding balls was used to prepare the nanoparticulate abiraterone acetate. In each experiment, 100 mg of pre-blended powder was added, the grinding vial was capped and the mixer mill was run for 20 minutes. The milled powder used for particle size analysis consisted of abiraterone acetate (30 mg), lactose monohydrate (68.5 mg) and sodium lauryl sulfate (1.5 mg). The milled powder used for dissolution studies consisted of abiraterone acetate (20 mg), lactose monohydrate (78.5 mg) and sodium lauryl sulfate (1.5 mg). In order to have enough material for dissolution testing, milled powder from several experiments was combined.

EXAMPLE 4. PARTICLE SIZE ANALYSIS OF MILLED AND UNMILLED ABIRATERONE ACETATE

Figure 3:
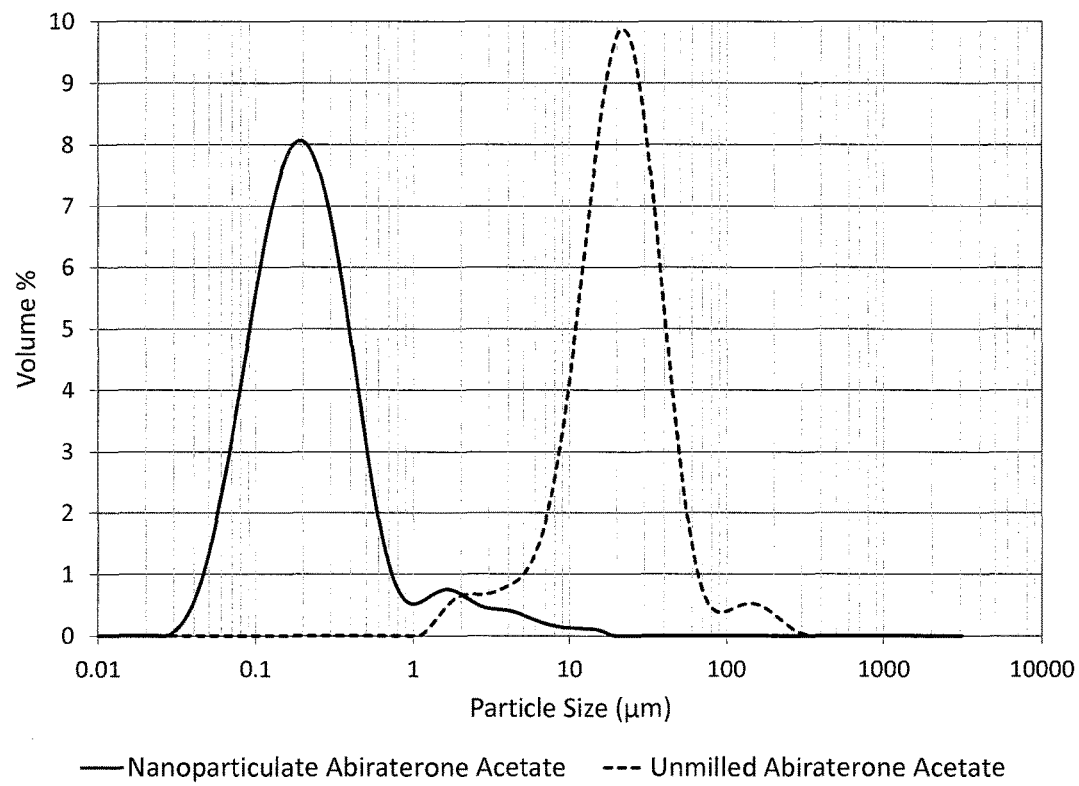
FIG. 3 is a graph depicting the dissolution of abiraterone acetate in a milled arbiraterone acetate composition from Example 3 and unmilled abiraterone acetate.

Milled powder samples from Example 3 were analyzed by adding 26 mg of milled material (6 mg of abiraterone acetate) to 5 ml of 0.1% w/w aqueous polyvinylpyrrolidone solution (PVP; BASF Kollidon® 30), then sonicating with an external sonication horn (Branson Digital Sonifier®) for 5 seconds at 20% amplitude followed by a 15 second pause. This cycle was continued until the total sonication time reached one minute. This suspension was then added dropwise to the sample cell of a Malvern Mastersizer 3000 particle size analyzer (Malvern Hydro MV pump unit) containing 125 ml of 0.1% PVP. The sample was then allowed to stir for 5 minutes prior to taking measurements. Data from the final measurements are presented in Table 1 and depicted graphically in FIG. 3.

For comparison, the particle size distribution of unmilled abiraterone acetate (raw drug substance) was also determined. The measurement conditions were similar as described above with the exception that the unmilled abiraterone acetate was added directly to the Malvern Hydro MV pump unit containing 130 ml of 0.1% PVP. 26 mg of unmilled abiraterone acetate had to be added directly to the Malvern pump unit in order to obtain obscuration values similar to that of the milled material. The abiraterone acetate was then subjected to 1 minute of bath sonication at 100% amplitude. The sample was then allowed to stir for 5 minutes prior to taking measurements. The data from these measurements are presented in Table 1 and depicted graphically in FIG. 3. The results indicate that the milled abiraterone acetate material contained nanoparticulate drug substance and that the size of the drug particles in the milled abiraterone acetate material was substantially smaller (greater than 10 times) than in the unmilled material. No nanoparticulate abiraterone acetate was measured in the unmilled drug sample.

Malvern Mastersizer 3000 Settings:

| Optical properties for abiraterone acetate: | Refractive Index: | 1.583 |
| | Absorption: | 0.01 |
| Optical properties for dispersant: | Refractive Index: | 1.33 |

Sample measurement time: 10 seconds

Background measurement time: 10 seconds

Number of measurement cycles: 3 (Results reported are an average of these)

Delay between cycles: 0

Stirrer setting: 2000 rpm

TABLE 1

Comparative particle size distribution data for milled and unmilled abiraterone acetate (volume statistics)

| | $D_{10}$ (µm) | $D_{50}$ (µm) | $D_{90}$ (µm) | D4,3 (µm) |
|---|---|---|---|---|
| Milled | 0.0858 | 0.215 | 0.657 | 0.490 |
| Unmilled | 8.18 | 21.8 | 47.3 | 28.1 |

EXAMPLE 5. DISSOLUTION OF MILLED AND UNMILLED ABIRATERONE ACETATE POWDER BLENDS

Figure 4:
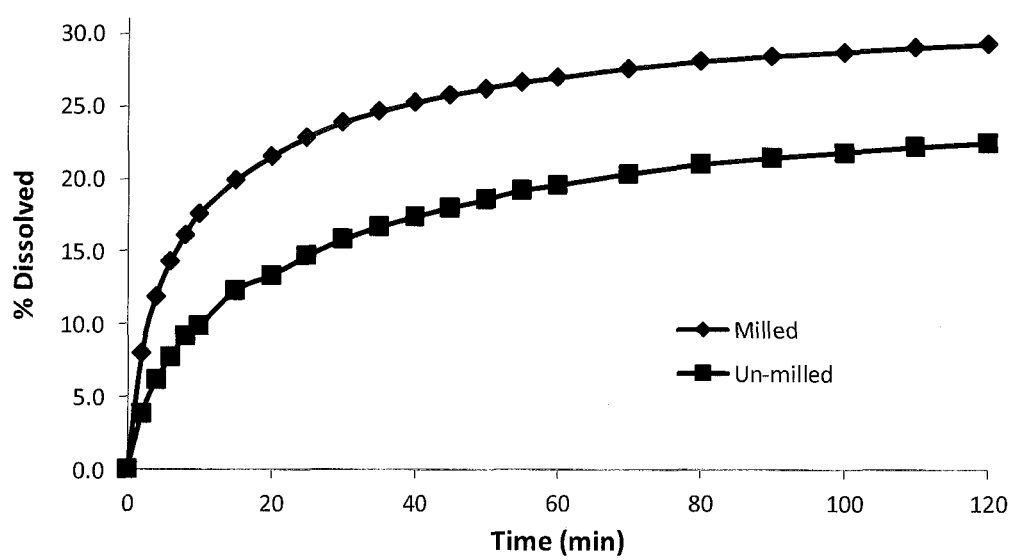
FIG. 4 is a graph depicting the size distribution of abiraterone acetate in a milled arbiraterone acetate composition from Example 1 and unmilled abiraterone acetate.

Dissolution behavior of the milled abiraterone acetate powder blend prepared in Example 3 was determined using an automated Sotax AT7 Smart dissolution testing unit fitted with a Thermo Fisher Scientific UV visible spectrometer (Model # EV0300 PC). The dissolution media was a 0.01 N HCl (pH=2) solution. The USP dissolution vessels were filled with 1000 ml of media and equilibrated to 37° C. The dissolution settings were according to USP type II apparatus with stirrer speed at 100 rpm. Two inline filters were utilized in series with pore sizes of 0.7 µm and 2.7 µm. The absorbance was measured at λ=236 nm. Dissolution studies were performed by adding duplicate samples of milled and unmilled abiraterone acetate powder blends directly to the dissolution media. The unmilled powder blend was identical in composition to the milled powder blend but was not processed in the mill. An abiraterone acetate dose of 100 mg was used for milled and unmilled samples which corresponded to a total powder weight of 500.0 mg. For the powder dissolution studies, measurements were taken at 2, 4, 6, 8, 10, 15, 20, 25, 30, 35, 40, 45, 50, 55, 60, 70, 80, 90, 100, 110 and 120 minutes. The dissolution results are plotted as percent of abiraterone acetate dissolved. The results of this comparative study are presented in Table 2 and illustrated graphically in FIG. 4. The results show that milled nanoparticulate abiraterone acetate dissolved more rapidly and to a greater percentage than the unmilled material.

TABLE 2

Comparative dissolution rates of milled nanoparticulate abiraterone acetate and unmilled abiraterone acetate (n = 2)

| | Milled Abiraterone acetate (%) | | Unmilled Abiraterone acetate(%) | |
|---|---|---|---|---|
| Time (min) | Average % Dissolved | Standard Deviation | Average % Dissolved | Standard Deviation |
| 0 | 0.0 | 0.0 | 0.0 | 0.0 |
| 2 | 8.0 | 0.0 | 3.8 | 0.3 |
| 4 | 11.9 | 0.7 | 6.2 | 0.5 |
| 6 | 14.3 | 1.0 | 7.7 | 0.6 |
| 8 | 16.1 | 0.9 | 9.2 | 0.6 |
| 10 | 17.6 | 1.1 | 9.9 | 0.0 |
| 15 | 19.9 | 0.7 | 12.3 | 1.0 |
| 20 | 21.5 | 0.5 | 13.3 | 0.6 |
| 25 | 22.8 | 0.3 | 14.7 | 0.9 |
| 30 | 23.8 | 0.2 | 15.8 | 0.8 |
| 35 | 24.6 | 0.1 | 16.7 | 0.7 |
| 40 | 25.2 | 0.2 | 17.3 | 0.4 |
| 45 | 25.7 | 0.3 | 18.0 | 0.3 |
| 50 | 26.2 | 0.4 | 18.6 | 0.2 |
| 55 | 26.6 | 0.6 | 19.2 | 0.1 |
| 60 | 26.9 | 0.7 | 19.5 | 0.1 |
| 70 | 27.6 | 0.8 | 20.3 | 0.2 |
| 80 | 28.0 | 0.9 | 21.0 | 0.2 |
| 90 | 28.4 | 1.0 | 21.4 | 0.3 |
| 100 | 28.7 | 1.0 | 21.8 | 0.3 |

TABLE 2-continued

Comparative dissolution rates of milled nanoparticulate abiraterone acetate and unmilled abiraterone acetate (n = 2)

| Time (min) | Milled Abiraterone acetate (%) | | Unmilled Abiraterone acetate(%) | |
|---|---|---|---|---|
| | Average % Dissolved | Standard Deviation | Average % Dissolved | Standard Deviation |
| 110 | 29.0 | 1.1 | 22.2 | 0.3 |
| 120 | 29.3 | 1.2 | 22.5 | 0.3 |

The invention claimed is:

1. A method of treating prostate cancer comprising administering methylprednisolone and a daily dose of between 400 and 600 mg of abiraterone acetate, wherein the abiraterone acetate is in the form of a tablet or a capsule and has a median particle size of 100 nm to 1000 nm on a volume average basis.

2. The method of claim 1 wherein the daily dose of abiraterone acetate is administered as a single dose.

* * * * *